United States Patent [19]

Wertheimer

[11] 4,134,679

[45] Jan. 16, 1979

[54] DETERMINING THE VOLUME AND THE VOLUME DISTRIBUTION OF SUSPENDED SMALL PARTICLES

[75] Inventor: Alan L. Wertheimer, North Wales, Pa.

[73] Assignee: Leeds & Northrup Company, North Wales, Pa.

[21] Appl. No.: 739,365

[22] Filed: Nov. 5, 1976

[51] Int. Cl.² .................... G01N 15/02; G01N 21/00; G01N 21/26
[52] U.S. Cl. ................................... 356/336; 250/574
[58] Field of Search ....................... 356/102, 103, 104; 350/574

[56] References Cited
U.S. PATENT DOCUMENTS

| 3,603,689 | 9/1971 | Shelnutt | 356/103 |
| 3,653,767 | 4/1972 | Liskowitz | 356/102 |
| 3,835,315 | 9/1974 | Gravitt | 356/103 X |
| 4,053,236 | 10/1977 | Atwood | 356/206 |

OTHER PUBLICATIONS

Barsic et al., Light Scattering: Polarization Ratio Methods, National Technical Information Service, pp. 167–174.

Primary Examiner—Conrad J. Clark
Assistant Examiner—Rodney B. Bovernick
Attorney, Agent, or Firm—William G. Miller, Jr.; Raymond F. MacKay

[57] ABSTRACT

A histogram of the volume of the particles in a sample of fluid-suspended particles, including those in the submicron region, can be obtained by using an incident light beam having a wavelength approximately twice the average particle diameter in each of the ranges of particle sizes making up the histogram. The 90° scatter from the sample is measured in two orthogonal polarizations. The first polarization has its electric vector perpendicular to the plane containing the point of observation and the incident light beam and the second is parallel to that plane. The magnitude of the light flux having the second polarization is subtracted from that having the first polarization in each range to give a measure of the volume of the particles in that range.

22 Claims, 6 Drawing Figures

$$a \left( a = \frac{\pi d}{\lambda} \right)$$

DETERMINING THE VOLUME AND THE VOLUME DISTRIBUTION OF SUSPENDED SMALL PARTICLES

BACKGROUND OF THE INVENTION

This invention relates to the measurement of the volume of small particles and the volume distribution of small particles. More particularly, the invention relates to the use of 90° scattering in the measurement of the volume of small particles in the range of approximately 0.1 to 10 microns in diameter, for example. In the past, there has been no reasonably accurate and simple method of determining the volume of small particles which include particles in the submicron region. This is particularly true with regard to the real time measurement of such particles which has become a necessity with the ever-increasing importance of real time measurement of particulate size in source emissions particularly in the size range from 0.1 to 10 microns in diameter. It is therefore an object of this invention to provide a method for making accurate measurements of the volume of small suspended particles and particularly a method of determining the volume distribution of small fluid suspended particles in different size ranges so as to be able to construct a histogram therefrom.

SUMMARY OF THE INVENTION

The volume of suspended small particles of a particular size or a particular size range is determined by passing through the sample a light beam and detecting the intensity of the light flux scattered by said particles at 90° from the axis of the incident light beam in both a first and second orientation of polarization. The light beam is of wavelength approximately twice the particle diameter where they are of one size or multiple wavelengths chosen to have twice the average particle diameter in the ranges of particle sizes of interest. The first orientation polarization has its electric vector perpendicular to the plane formed by the direction of propagation of the incident light beam and the point of observation and the second orientation of polarization has its electric vector parallel to that plane. The detected intensity of the light polarized in the second orientation is subtracted from the detected intensity of the light polarized in the first orientation to give a resulting value which is proportional to the volume of the particles or, in the case of a group of particles, the average volume of the particles.

BRIEF DESCRIPTION OF THE DRAWINGS

The invention is illustrated in the following Figures in which like reference characters represent like elements.

DESCRIPTION OF THE PREFERRED EMBODIMENTS

For visible light, the majority of the 0.2 to 10 micron diameter range must be treated by a complete and rigorous theory first discussed by Mie and referred to as "Mie scattering". In this theoretical treatment, the exact size of the particle plays an important role. For spherical particles, the wavelength is usually expressed through the dimensionless quantity, $a = \pi d/\lambda$, with d representing the diameter of the particles and lambda the wavelength of the light beam interacting with the particles. Within this realm, other parameters figure significantly in the characterization of scattering. These include the refractive index, both real and complex portions, and the polarization of the incident light.

Figure 1:
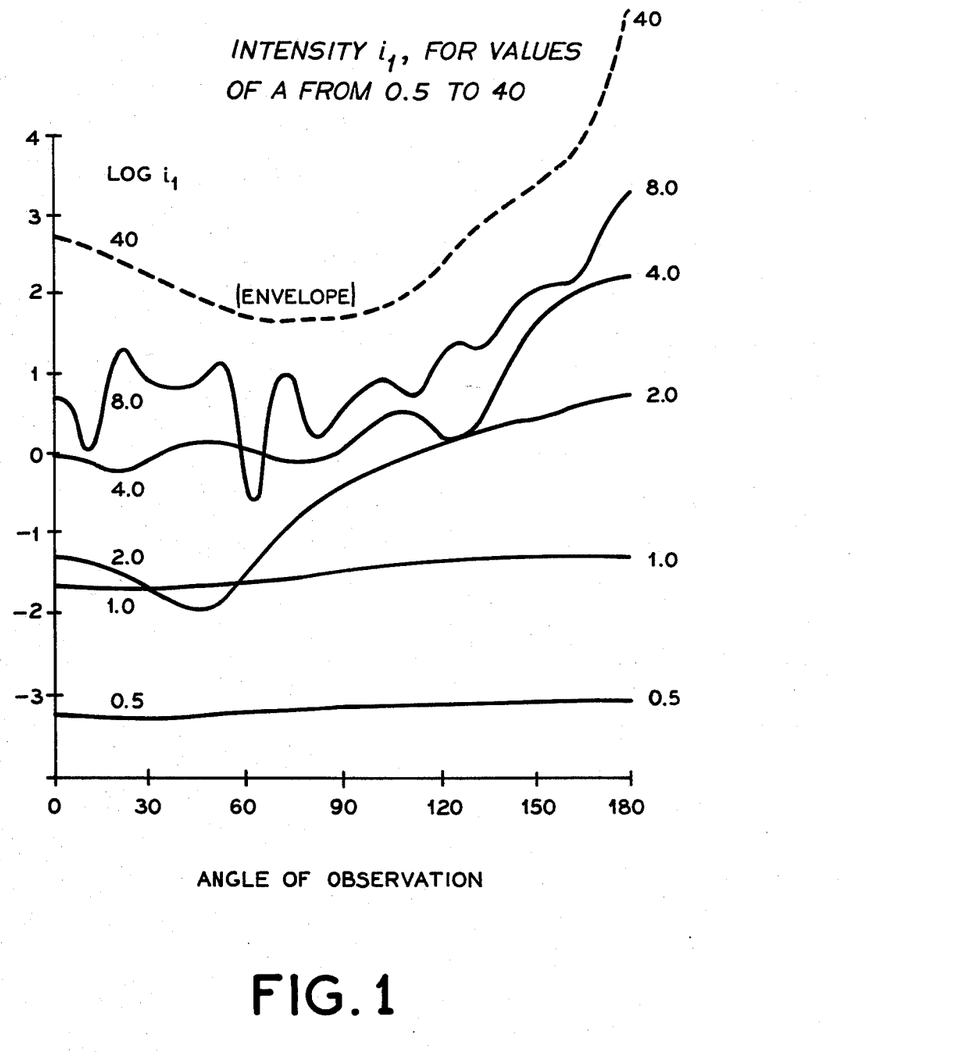
FIG. 1 is a drawing showing the intensity of the light flux scattered by a particle and polarized in a direction perpendicular to the plane of observation over a range of angles of observation for various ratios of the particle diameter to the light wavelength.
Figure 2:
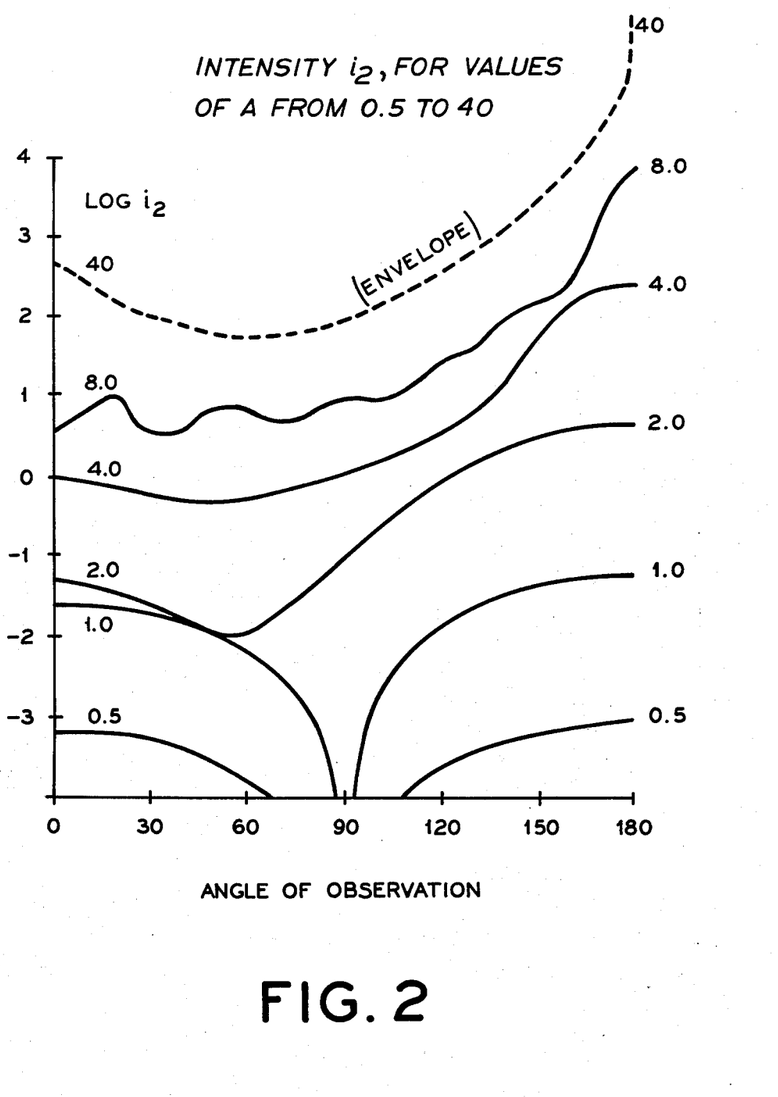
FIG. 2 is another set of curves similar to FIG. 1 showing the intensity of the light flux polarized parallel to the plane of observation.

Mie theory has been studied extensively and numerous tables of the angular distribution of flux have been prepared by others for use with problems of this nature. In order to illustrate some characteristics of the angular distribution of flux, FIG. 1 and FIG. 2 show a plot of tabulated data from $a = 0.5$ to 40 for spherical particles with an index of refraction relative to the surrounding medium of 1.33. Two orthogonal polarizations are shown. They are referred to as $i_1$ and $i_2$. FIG. 1 shows the intensity of a light flux in one polarization $i_1$ for values of "a" from 0.5 to 40 over an angle of observation from 0 to 180 degrees, whereas FIG. 2 shows the intensity of the light flux polarized in an orthogonal direction; namely, $i_2$ for values of "a" from 0.5 to 40 over the same range of angles of observation; namely, from 0 to 180 degrees. The orientation of polarization of $i_1$ is perpendicular to the plane of observation defined by the incident light path and the point of observation of the scattered light while the orientation of polarization of $i_2$ is in the plane of observation.

It may be noted that one of the more stable characteristics of the patterns, as shown in FIGS. 1 and 2, for different indices of refraction is the null at 90° for $i_2$ at small values of "a". It should be mentioned that these curves, namely FIG. 1 and FIG. 2, describe the light scattered from individual particles. A suspension of N identical particles widely separated from each other would produce an angular pattern N times as intense as that of a single particle if no significant shadowing or secondary scattering occurs. This assumption is referred to as single scattering.

FIG. 1 and FIG. 2 illustrate significant differences between the intensities measured at 90° for two orthogonal polarizations of light. For a range of values of "a" from 0.5 to 40, the difference in intensity can be calculated by subtracting values taken from the two curves at the 90° point. The percentage change is greatest for $a = 0.5$ and 1.0 since for those $i_2$ goes to 0 at 90°, although the absolute value of the difference per particle generally increases as the particle diameter increases.

Figures 3, 4:
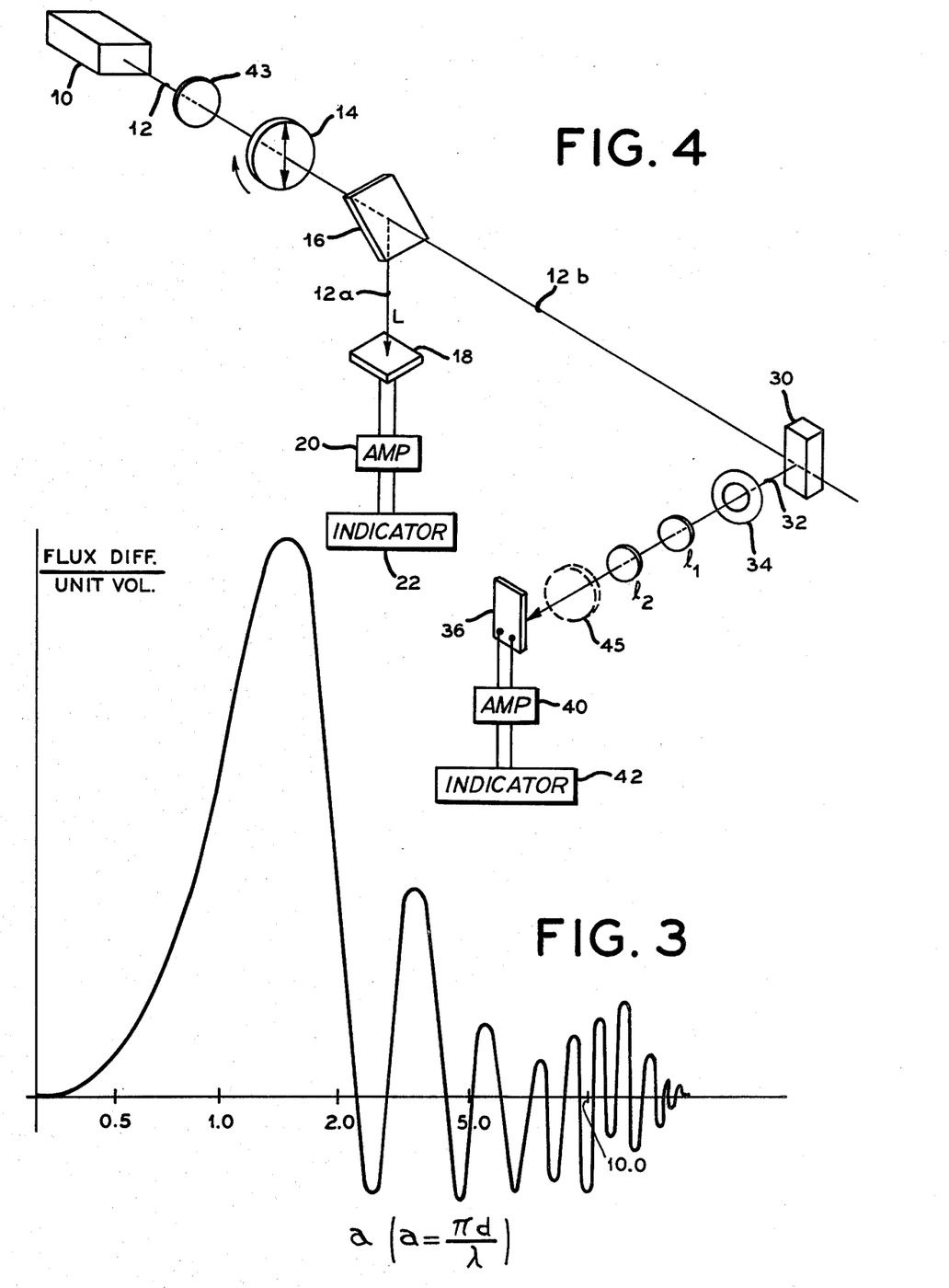
FIG. 3 is a characteristic showing the relationship of the flux difference per unit volume of a particle for 90° scattering over a range of ratios of particle diameter to light wavelength.
FIG. 4 is a block diagram (with the light path shown in perspective) showing an arrangement of apparatus for making the measurements necessary to determine the volume of small particles in a particular sample.

I have found that if one plots the flux difference per unit volume for a particle ($i_1$ minus $i_2$ divided by the volume of the particle) against "a", a curve is obtained which has a well-defined peak where "a" is approximately 1.5 or 1.6, as shown in the normalized response curve of FIG. 3. It will also be noted that the half-width of the peak covers approximately a range of a = 1 to a = 2. Based on the response curve of FIG. 3 and particularly that part of the curve exhibiting the peak, it can be seen that it is possible to determine the volume of particles of any certain size if a light beam of a specific wavelength (approximately $\pi/1.5$ or twice the particle diameter) is used to measure $i_1$ and $i_2$. When the light source has a changing bias in polarization, the difference $i_1/L_1 - i_2/L_2$ may advantageously be measured to eliminate the effect of the source variations. Thus, using a light source of a particular wavelength and measuring the light flux scattered at 90° in two orthogonal polarization planes, it is possible to determine by virtue of the value of the difference between those two flux measurements the volume of the particles of a particular size or in a particular size range. When a range of particle sizes is to be measured, the range may be represented by the range of values of "a" between the half-width points of the peak, the 50% range. An example of the ranges over which a response can be obtained as a function of wavelength to obtain a histogram, for example, is shown by the following table:

TABLE 1

| Wavelength | Particle Diameter at Peak of Response | 50% Range |
|---|---|---|
| 0.4 microns | 0.2 microns | .13 to .25 microns |
| 0.6328 microns* | 0.3 microns | .20 to .40 microns |
| 1.06 microns* | 0.5 microns | .34 to .67 microns |
| 1.25 microns | 0.6 microns | .40 to .80 microns |
| 2.2 microns | 1.05 microns | .70 to 1.4 microns |
| 5.0 microns | 2.39 microns | 1.6 to 2.3 microns |
| 10.6 microns* | 5.06 microns | 3.4 to 6.7 microns |
| 11.6 microns | 5.5 microns | 3.7 to 7.4 microns |

*Fundamental Laser Wavelengths

The figures in the table are, of course, for a specific refractive index; namely, 1.33. Other indices produce slightly different curves than those shown in FIGS. 1 and 2, although the basic characteristic is preserved. The curve corresponding to FIG. 3 as it would apply to glass spheres having a refractive index of 1.55 would be similar to the curve in FIG. 3, for it would have its peak at approximately the same value; namely, "a" between 1.5 and 1.6, although the shape of the curve will, to some extent, be determined by the composition of the material in the sample being measured. Where a number of ranges of particle sizes are to be measured, as in the construction of a histogram, the same curve of FIG. 3 would apply to the measurements in each range of particulate sizes and to a first approximation the relative contribution of the particles of different composition in each range would be the same. Thus, the measurement is substantially insensitive to the particular composition of the particulate matter in the sample. In constructing the histogram it may be desirable to make the first measurement with a light source wavelength corresponding to that required for the largest particle present in the sample. Then each successive measurement would utilize the next shortest wavelength. By following such a sequence, the response to the positive and negative portions of the characteristic of FIG. 3 above a = 2 can be compensated for in the measurement for each subsequently measured range.

In FIG. 4 there is shown an example of an apparatus which can be utilized for making the volume measurement described above. In this apparatus there is utilized a light source 10 such as an incandescent source or a laser. The source includes any optics necessary to produce the light beam 12 which passes through a polarizing element 14 for selectively changing the polarization of the light beam 12. The polarizing element 14 may be a rotating Glan prism which can be rotated through one quarter turn about the optical axis, for example, to sequentially obtain the polarization of light beam 12 in the two orthogonal directions as necessary for this measurement. The element 14 is shown in one position in FIG. 4 as necessary to polarize the beam 12 so that its electric vector is oriented as indicated by the double ended arrow.

The light beam 12 is passed through a beam splitter 16 and part of the beam 12a is diverted towards detector 18. Detector 18 measures the intensity L of the beam 12a by producing a signal through amplifier 20 to the indicator 22 which indicates the intensity of the light flux in light beam 12a. This intensity measurement may be used as a reference for the measurement of the volume of the particulates in that the measurement as indicated by indicator 22 will vary directly with the variation in the intensity of the light source 10.

That portion of the light beam which goes straight through the beam splitter 16 is shown as light beam 12b. That light beam (the incident beam) impinges or is incident upon the sample in container 30 which may, for example, be a cuvette containing a sample of fluid suspended particles. A portion of the light beam will go through the cuvette while a portion of the light beam will be scattered from the particles in the cuvette 30. That portion of the scattered light which is scattered at 90° from the incident beam and preferably within a cone of a few degrees about the 90° path is indicated as the scattered light in path 32. The light in path 32 may be directed through a diaphragm such as 34 and then through lens such as $l_1$ and $l_2$ as may be required to focus the scattered light on detector 36 at the point of observation. Other flux collecting devices, such as curved mirrors, may also be used to focus the scattered light. The intensity of the light flux is measured at 36 and a signal indicative of the measured value is transmitted to amplifier 40 for amplification and transmission to indicator 42 where the value is displayed.

In order to determine an intensity measurement equal to $i_1$, the rotating polarizing element 14 is positioned so that the light beam 12 is polarized so that its electric field is perpendicular to the plane defined by the axis of propagation of incident light beam 12b and the point of observation; namely, detector 36. In FIG. 4 that plane is the plane defined by beam 12b and path 32 and the electric field is in the direction shown. With the polarizing element in that position, a measurement is made by observing indicator 42 to give a value for $i_1$.

There is then obtained a value for $i_2$ by rotating polarizing element 14 about the axis of beam 12 by 90° so as to rotate the plane of polarization of the incident light beam 12 to the plane defined by the axis of propagation of the incident light beam 12b and the pointed observation. With the element 14 so positioned, the indication provided by the indicator 42 is observed to give a value for $i_2$.

The values of $i_1$ and $i_2$ are then compared by subtracting $i_2$ from $i_1$ to obtain the flux difference for the scattered light intensity at 90° to the incident beam for the two separate orthogonal directions. That flux difference measurement is then a measure of the volume of the particles in the particular range of interest as determined by the wavelength of the light source 10 utilized in making the measurement. If the intensity of the light source 10 varies, such variations can be compensated for by dividing the flux difference ($i_1 - i_2$) by L to obtain a measure of the volume of the particles independent of the intensity changes in the source 10.

If discrete laser wavelengths are used as different light sources at 10, there is then no requirement to use a monochromatic filter in the light path; however when an incandescent or thermal source is used for source 10, it becomes necessary to insert a monochromatic filter 43 in the beam produced by the source or a similar filter 45 in the scattered light path to limit the wavelength of the light used for the measurement to a particular known value.

For making a series of measurements to determine the volume of particles in different size ranges such as tabulated in Table 1 as the 50% ranges, it is, of course, necessary to make the measurements to determine $i_1$ and $i_2$ for each of several light source wavelengths as determined by the source alone in the case of a laser or by changing a monochromatic filter in the light path when a thermal source is used. As shown in Table 1, eight different ranges of particle size ranging from 0.13 to 7.4 microns can be covered by using eight different wavelengths of light for the incident beam.

Figure 5:
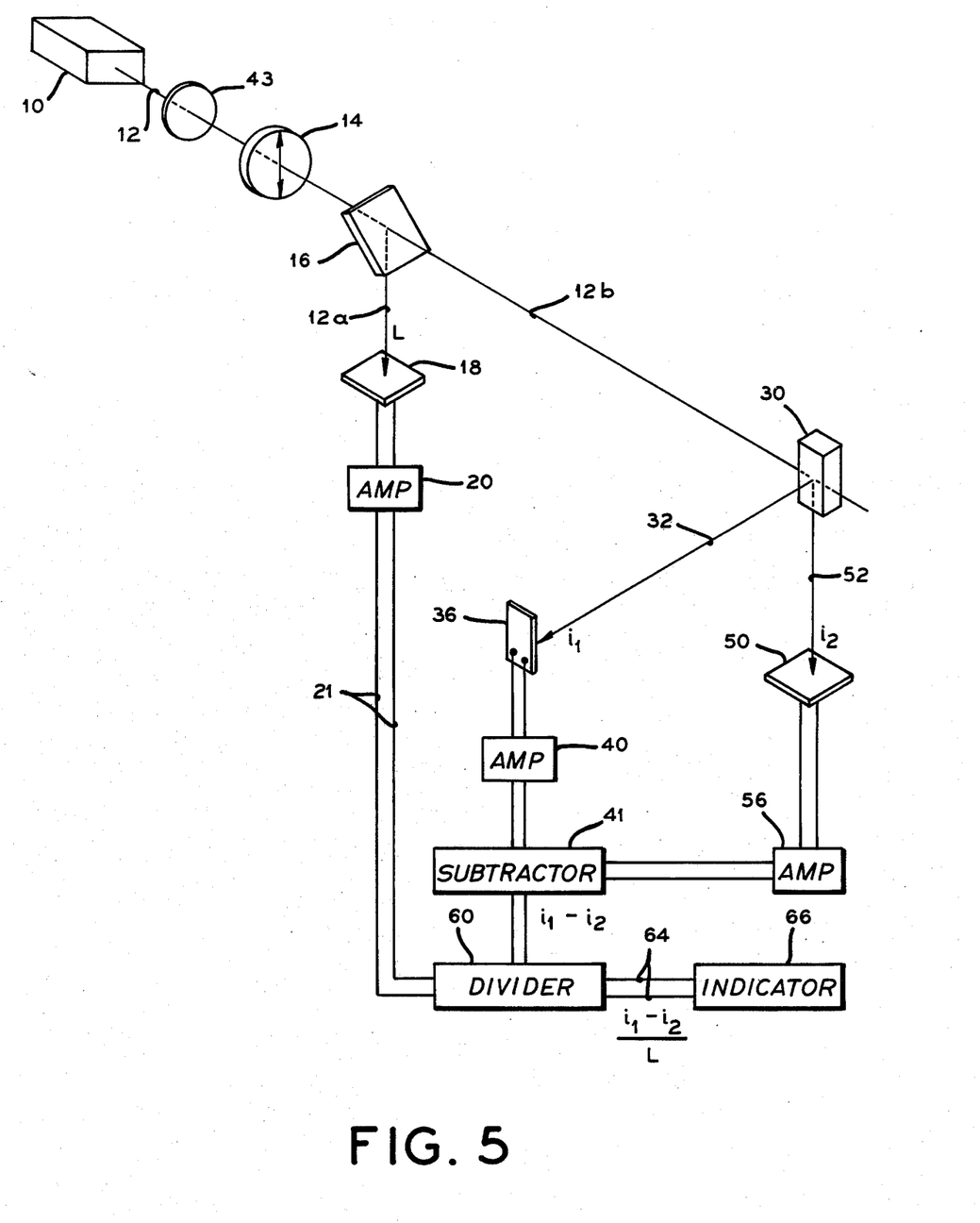
FIG. 5 is a diagram showing another arrangement of apparatus suitable for continuous monitoring.

FIG. 5 shows apparatus capable of supplying a continuous indication of the flux difference compensated for variations in the intensity of the incident beam. The light source 10 which may be assumed to be an incandescent source, for example, produces a light beam 12 which passes through the monochromatic filter 43 and thence through a polarizer 14 and the beam splitter 16. The light beam 12a is created by the beam splitter 16 and impinges on the detector 18 which detects the intensity of the light beam and therefore provides an indication by way of amplifier 20 and its output lines 21 of the magnitude L of the flux emitted by the light source 10 in beam 12. The portion of the beam which continues through the beam splitter 16, namely the beam 12b, impinges on the particles in the sample container 30 as the incident light beam. Light is scattered from the particles in the sample in accordance with the principles set forth by Mie and illustrated in FIGS. 1-3.

In FIG. 5 the scattered light that is observed is that appearing on each of two paths which are at 90° with reference to the incident light beam 12b. Additionally, these paths of observation 32 and 52 are orthogonal one to the other. Thus, it will be seen that one of the paths of observation, path 32, which is observed by detector 36 detects the scattered light along the path 32 that is polarized in a direction perpendicular to the plane of observation which in this case is defined by the axis of beam 12b and the point of observation at detector 36. The polarization of the beam 12 remains fixed in the direction indicated by the arrows in the polarizer 14. The detector 36 thus detects the intensity $i_1$ of the light which has a direction of polarization perpendicular to the observation plane. The value of $i_1$ is amplified by amplifier 40 and transmitted to the subtractor 41 as one input thereof.

The other point of observation of the scattered light is that established by the detector 50 which detects the light scattered along the path 52 which passes light polarized in the observation plane defined by the incident light beam axis 12b and the observation point at detector 50. The magnitude of the light detected by the detector 50 is of a value corresponding to $i_2$ and is amplified by amplifier 56 and thence provided as another input to subtractor 41.

The subtractor 41 then calculates the quantity $i_1 - i_2$ and that value is transmitted to the ratio calculating unit 60 as one input thereof. The other input to the unit 60 is provided from lines 21 giving an indication of the magnitude of the total light from light source 10. The ratio calculated by the unit 60 is then provided on the output lines 64 to the indicator 66 as a quantity $(i_1 - i_2)/L$. By dividing the difference between the intensities $i_1$ and $i_2$ by the intensity of the light source 10, it is possible to eliminate variations in the indicated value as produced by indicator 66 as might occur due to any variation of intensity of the light source 10 with time.

As will be evident to those skilled in the art, the arrangement of FIG. 4 has aspects which are advantageous in the calculation of the volume of the particles in the sample in that a single detector only is used and it is not necessary to take into account the different sensitivities of the detectors 36 and 50 in FIG. 5. However, it will be evident also that the arrangement of FIG. 5 can provide a continuous monitoring of the volume of the particles in the sample 30 which would be advantageous for applications in which that sample may be a flowing sample rather than a static sample.

With regard to FIG. 5, the monochromatic filter 43 may, of course, be dispensed with whenever the light source utilized is a laser instead of a thermal source. Also, it should be noted that the monochromatic filter 43 may be removed from the incident light beam and placed in the scattered light path such as the path 32 and path 52 so that the scattered light is filtered rather than the incident light when a thermal source is used as the source 10.

It is, of course, obvious that the paths 32 and 52 can include optical elements such as the diaphragm 34 and lenses $l_1$ and $l_2$ (or mirrors) as may be required to provide a focusing of the scattered light received along paths 32 and 52.

Figure 6:
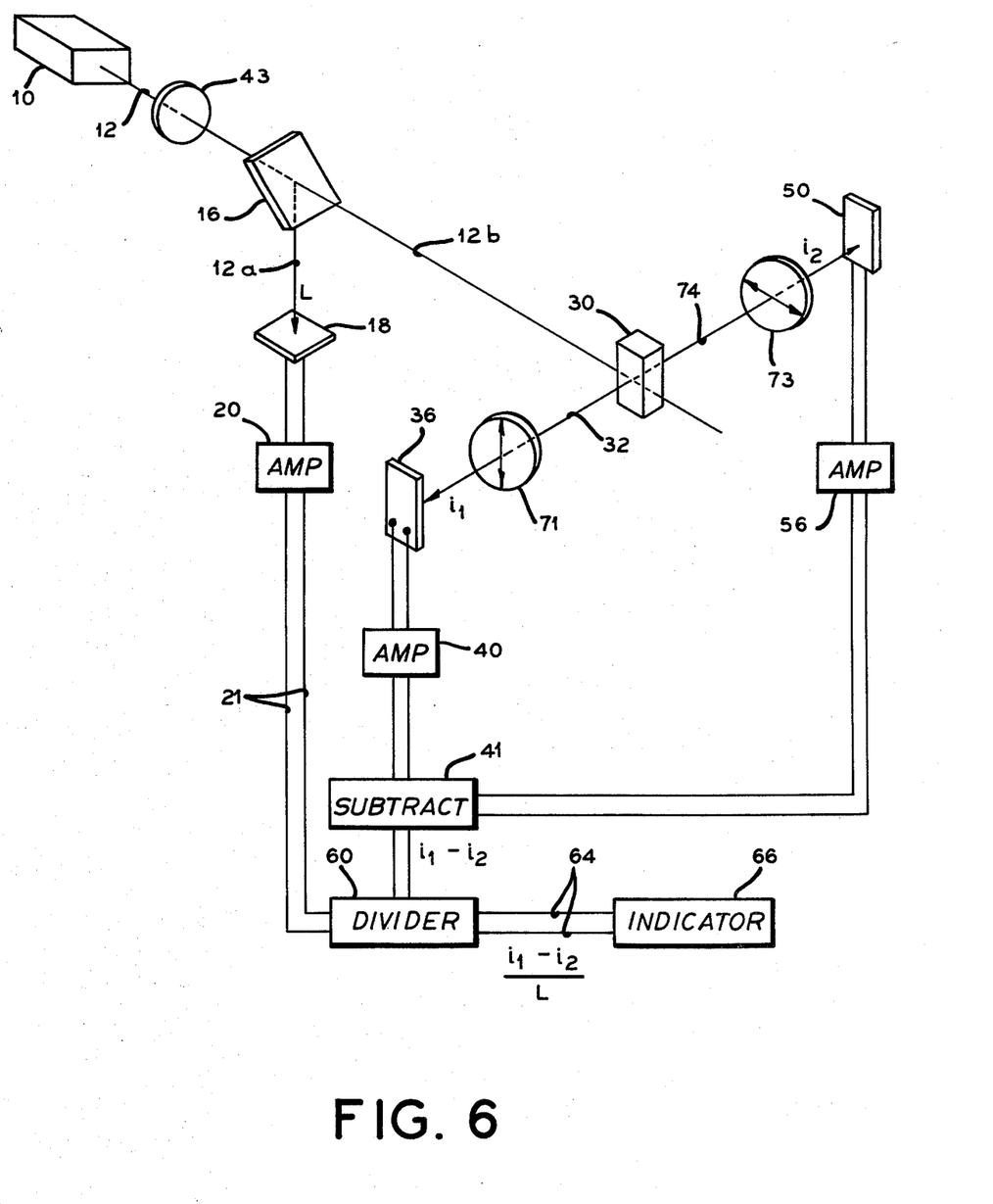
FIG. 6 is a diagram showing still another arrangement of apparatus for continuous monitoring.

FIG. 6 shows an apparatus similar to that described in FIG. 5 except that the incident light is unpolarized and the observed scattered light paths are in the same plane with the light in those paths being polarized in orthogonal directions. Thus, polarizer 14 of FIG. 5 is omitted and is replaced in path 32 by polarizer 71 which is arranged to pass light polarized in the direction perpendicular to the observation plane to provide a light intensity $i_1$ at detector 36.

The other observation point at detector 50 in path 74 is in the same plane with path 32. The path 74 includes polarizer 73 to pass to detector 50 only light polarized in a direction parallel to the observation plane and hence the light intensity $i_2$ is detected by detector 50. Both polarizers 71 and 73 normally will remain fixed.

What is claimed is:

1. The method of determining the total volume of the particles in a sample of suspended particles of a particular size comprising the steps of:

directing at said sample an incident light beam;

separately detecting the intensity of that light flux having a wavelength equal to approximately twice the diameter of said particles as scattered by said particles at 90° from the axis of said incident light beam in first and second orthogonal polarizations, said first polarization being perpendicular to the plane of observation as defined by the axis of propagation of said incident beam and the point of observation, and said second polarization being parallel to said plane; and subtracting the intensity of the light flux detected as having the second polarization from that detected as having the first polarization to obtain a resulting value proportional to the total volume of said particles.

2. A method according to claim 1, wherein the same plane of observation is employed for each intensity detection.

3. A method according to claim 1, wherein the incident beam is plane polarized and the separate detections are performed at points of observation so located that the two polarizations exist in the scattered light at these points respectively.

4. The method of determining for a sample of suspended particles the volume distribution of the particles in different size ranges, comprising the steps of:
directing at different times an incident beam of light of different wavelengths through said sample, the different wavelengths of said light beam each being associated with a different one of said ranges such that said wavelengths are approximately twice the diameter of the average particle size in said ranges;
separately detecting for each of the different light beam wavelenghts the intensity of the light flux scattered by said particles at 90° from the axis of said incident light beam in first and second orthogonal polarizations, said first polarization being perpendicular to the plane of observation as defined by the axis of said incident beam and the point at which the light flux is being detected, and said second polarization being parallel to said plane; and
subtracting the intensity of the light flux detected as having said second polarization from that detected as having said first polarization to obtain for each wavelength a resulting value proportional to the total volume of the particles in the corresponding size range.

5. A method according to claim 4, wherein the separate detections are performed in sequence at the same point of observation at which the two polarizations are established by correspondingly polarizing the incident beam.

6. A method according to claim 4, wherein the separate detections are performed at two points of observation at which the two polarizations are established by polarizers in the path of the scattered light, the incident beam being unpolarized.

7. The method of determining for a sample of suspended particles the volume distribution of suspended particles in a particular size range, comprising the steps of:
directing at said sample an incident beam of light, the wavelength of said light beam being approximately twice the diameter of the average particle size in said range;
separately detecting the intensity of the light flux scattered by said particles at 90° from the axis of said incident light beam in both first and second orthogonal polarizations, said first polarization being perpendicular to the plane of observation as defined by the axis of said incident beam and the point at which the scattered light is being detected and said second polarization being parallel to said plane; and
subtracting the intensity of the light flux detected as having said second polarization from that detected as having the first polarization to obtain a resulting value proportional to the total volume of the particles in said size range.

8. The method of determining the volume of the total particles in a sample of suspended particles of a particular size, comprising the steps of:
directing a light beam along a path incident to said sample;
detecting the intensity of that light whose wavelength is approximately twice the diameter of said particles that is scattered by said particles along a path at right angles to said incident path and polarized in a first orientation perpendicular to the plane of observation associated with said detection;
detecting the intensity of the light of said wavelength as scattered by said particles along a path at right angles to said incident path and polarized in a second orientation parallel to the plane of observation associated with said last mentioned detection; and
subtracting the intensity of the scattered light detected as being polarized in said second orientation from the intensity of the scattered light detected as being polarized in said first orientation to produce a difference of value related to the total volume of said particles.

9. The method of claim 8 which includes the steps of:
detecting the intensity of the incident light beam; and
dividing the difference by the intensity of the incident light beam.

10. The method of determining the volume of the total particles in a sample of suspended particles of a particular size, comprising the steps of:
directing a light beam along a path incident to said sample;
detecting the intensity of that light whose wavelength is approximately twice the diameter of said particles that is scattered by said particles along a path at right angles to said incident path and polarized in a first orientation perpendicular to the plane of observation associated with said detection;
detecting the intensity of the incident light beam during detection of the intensity of the scattered light polarized in the first orientation;
dividing the intensity of the scattered light polarized in the first orientation by the simultaneously detected intensity of the incident light beam;
detecting the intensity of the light of said wavelength as scattered by said particles along a path at right angles to said incident path and polarized in a second orientation parallel to the plane of observation associated with said last mentioned detection;
detecting the intensity of the incident light beam during detection of the intensity of the scattered light polarized in the second orientation;
dividing the intensity of the scattered light polarized in the second orientation by the simultaneously detected intensity of the incident light beam; and
subtracting the values resulting from said divisions to produce a difference of value related to the total volume of said particles.

11. Apparatus for determining the total volume of the particles in a sample of suspended particles of a particular size comprising:
means for directing at said sample an incident light beam;
means for separately detecting the intensity of that light flux having a wavelength equal to approximately twice the diameter of said particles as scattered by said particles at 90° from the axis of said incident light beam in first and second orthogonal polarizations, said first polarization being perpendicular to the plane of observation as defined by the exis of propagation of said incident beam and the point of observation, and said second polarization being parallel to said plane; and means for subtracting the intensity of the light flux detected as having the second polarization from that detected as having the first polarization to obtain a resulting value proportional to the total volume of said particles.

12. Apparatus for determining for a sample of suspended particles the volume distribution of the particles in different size ranges, comprising:

means for directing at different times an incident beam of light of different wavelengths through said sample, the different wavelengths of said light beam each being associated with a different one of said ranges such that said wavelengths are approximately twice the diameter of the average particle size in said ranges;

means for separately detecting for each of the different light beam wavelengths the intensity of the light flux scattered by said particles at 90° from the axis of said incident light beam in first and second orthogonal polarizations, said first polarization being perpendicular to the plane of observation as defined by the axis of said incident beam and the point at which the light flux is being detected, and said second polarization being parallel to said plane; and means for subtracting the intensity of the light flux detected as having said second polarization from that detected as having said first polarization to obtain for each wavelength a resulting value proportional to the total volume of the particles in the corresponding size range.

13. Apparatus for determining for a sample of suspended particles the volume distribution of suspended particles in a particular size range, comprising:

means for directing at said sample an incident beam of light, the wavelength of said light beam being approximately twice the diameter of the average particle size in said range;

means for separately detecting the intensity of the light flux scattered by said particles at 90° from the axis of said incident light beam in both first and second orthogonal polarizations, said first polarization being perpendicular to the plane of observation as defined by the axis of said incident beam and the point at which the scattered light is being detected and said second polarization being parallel to said plane; and means for subtracting the intensity of the light flux detected as having said second polarization from that detected as having the first polarization to obtain a resulting value proportional to the total volume of the particles in said size range.

14. Apparatus for determining the total volume of the particles in a sample of suspended particles of a particular size, comprising:

means for directing a light beam along a path incident to said sample;

means for detecting the intensity of that light whose wavelength is approximately twice the diameter of said particles that is scattered by said particles along a path at right angles to said incident path and polarized in a first orientation perpendicular to the plane of observation associated with said detection;

means for detecting the intensity of the light of said wavelength as scattered by said particles along a path at right angles to said incident path and polarized in a second orientation parallel to the plane of observation associated with said last-mentioned detection; and means for subtracting the intensity of the scattered light detected as being polarized in said second orientation from the intensity of the scattered light detected as being polarized in said first orientation to produce a difference of value related to the total volume of said particles.

15. Apparatus as set forth in claim 14 which includes:

means for detecting the intensity of the incident light beam; and dividing the difference by the intensity of the incident light beam.

16. The method of determining in a sample of suspended particles the total volume of the particles of a particular size range around an average diameter comprising the steps of:

directing at said sample an incident light beam;

separately producing signals varying with the intensity of that light flux having a wavelength equal to approximately twice the average diameter as scattered by particles along a path whose axis is at 90° from the axis of said incident light beam in first and second orthogonal polarizations, said first polarization being perpendicular to the plane of observation as defined by the axis of propagation of said incident beam and the point of observation, and said second polarization being parallel to said plane; and subtracting the signal varying with the light flux detected as having the second polarization from the signal varying with the light flux detected as having the first polarization to obtain a resulting signal of value proportional to the total volume of said particles.

17. The method of determining in a sample of suspended particles the total volume of the particles of a particular size range around an average diameter comprising the steps of:

directing at said sample an incident light beam;

separately detecting the intensity of that light flux having a wavelength equal to approximately twice the average diameter as scattered by said particles along a path whose axis is at 90° from the axis of said incident light beam in first and second orthogonal polarizations, said first polarization being perpendicular to the plane of observation as defined by the axis of propagation of said incident beam and the point of observation, and second polarization being parallel to said plane; and subtracting the intensity of the light flux detected as having one of said polarizations from that detected as having the other of said polarizations to obtain a resulting value proportional to the total volume of said particles.

18. Apparatus for determining for a sample of suspended particles the volume distribution of the particles in different size ranges, comprising:

means for directing at different times an incident beam of light of different wavelengths through said sample, the different wavelengths of said light beam each being associated with a different one of said ranges such that said wavelengths are approximately twice the diameter of the average particle size in said ranges;

means for separately producing for each of the different light beam wavelengths signals varying in intensity with the light flux scattered by said particles along a path whose axis is at 90° from the axis of said incident light beam in first and second orthogonal polarizations, said first polarization being perpendicular to the plane of observation as defined by the axis of said incident beam and the point at which the light flux is being detected, and said second polarization being parallel to said plane; and means for subtracting said signal varying with the intensity of the light flux detected as having said second polarization from the signal varying with the intensity of the light flux detected as having said first polarization to obtain for each wavelength a resulting signal proportional to the total volume of the particles in the corresponding size range.

19. Apparatus for determining for a sample of suspended particles the volume distribution of the particles in different size ranges, comprising:

means for directing at different times an incident beam of light of different wavelengths through said sample, the different wavelengths of said light beam each being associated with a different one of said ranges such that said wavelengths are approximately twice the diameter of the average particle size in said ranges;

means for separately detecting for each of the different light beam wavelengths the intensity of the light flux scattered by said particles along a path whose axis is at 90° from the axis of said incident light beam in first and second orthogonal polarizations, said first polarization being perpendicular to the plane of observation as defined by the axis of said incident beam and the point at which the light flux is being detected, and said second polarization being parallel to said plane; and means for substracting the intensity of the light flux detected as having one of said first and second polarizations from that detected as having the other of said polarizations to obtain for each wavelength a resulting value proportional to the total volume of the particles in the corresponding size range.

20. Apparatus as set forth in claim 19 which includes:

means for producing a signal varying with the intensity of the incident light beam; and means for dividing said resulting signal by said signal varying with the incident light beam.

21. The method of determining the total volume of the particles of a particular size suspended in a sample comprising the steps of:

directing at said sample an incident light beam;

separately detecting the intensity of that light flux having a wavelength equal to approximately twice the diameter of said particles as scattered by said particles along a path as 90° from the axis of said incident light beam in first and second orthogonal polarizations, said first polarization being perpendicular to the plane of observation as defined by the axis of propagation of said incident beam and the point of observation, and said second polarization being parallel to said plane; and determining the total volume of said particles in accordance with the difference between a quantity varying with the intensity of the light flux detected as having one of said polarizations and a quantity varying with the intensity of the light flux detected as having the other of said polarizations.

22. Apparatus for determining in a sample of suspended particles the total volume of particles in a particular size range around an average diameter comprising:

means for directing at said sample an incident light beam;

means for separately detecting the intensity of that light flux having a wavelength equal to approximately twice the average diameter as scattered by said particles at 90° from the axis of said incident light beam in first and second orthogonal polarizations, said first polarization being perpendicular to the plane of observation as defined by the axis of propagation of said incident beam and the point of observation, and said second polarization being parallel to said plane; and means for determining the total volume of said particles in accordance with the difference between a quantity varying with the intensity of the light flux detected as having one of said polarizations and a quantity varying with the intensity of the light flux detected as having the other polarization.

* * * * *